US009435200B2

(12) United States Patent
Goodwin

(10) Patent No.: US 9,435,200 B2
(45) Date of Patent: Sep. 6, 2016

(54) DETERMINATION OF THERMODYNAMIC PROPERTIES OF A FLUID BASED ON DENSITY AND SOUND SPEED

(75) Inventor: Anthony Robert Holmes Goodwin, Sugar Land, TX (US)

(73) Assignee: SCHLUMBERGER TECHNOLOGY CORPORATION, Sugar Land, TX (US)

(*) Notice: Subject to any disclaimer, the term of this patent is extended or adjusted under 35 U.S.C. 154(b) by 600 days.

(21) Appl. No.: 13/364,750

(22) Filed: Feb. 2, 2012

(65) Prior Publication Data

US 2013/0204533 A1    Aug. 8, 2013

(51) Int. Cl.
| | |
|---|---|
| *G01N 25/18* | (2006.01) |
| *G01K 17/06* | (2006.01) |
| *G01K 13/02* | (2006.01) |
| *G06F 17/40* | (2006.01) |
| *G06F 19/00* | (2011.01) |
| *E21B 49/10* | (2006.01) |
| *E21B 49/08* | (2006.01) |

(52) U.S. Cl.
CPC ............. *E21B 49/10* (2013.01); *G01K 13/02* (2013.01); *G01K 17/06* (2013.01); *G01N 25/18* (2013.01); *E21B 2049/085* (2013.01); *G06F 17/40* (2013.01); *G06F 19/00* (2013.01)

(58) Field of Classification Search
CPC .. E21B 49/10; E21B 17/07; E21B 2049/085; E21B 28/00; E21B 36/04; E21B 41/00; E21B 44/00; E21B 44/005; E21B 49/08; E21B 49/081; G01N 33/2823; G01N 1/14; G01N 2001/2064; G01N 2291/02818; G01N 2291/02872; G01N 2291/044; G01N 29/024; G01N 29/227; G01N 33/24; G01N 7/00; G01N 7/16; G01N 9/002; G01N 9/24; G01N 9/26; G01N 9/36; F17D 3/10; G01F 1/58; G01V 13/00; G06F 17/00
USPC .................. 73/1.01–1.89, 19.01–19.12, 73/23.2–31.07, 36, 37, 37.5
See application file for complete search history.

(56) References Cited

U.S. PATENT DOCUMENTS

| | | | |
|---|---|---|---|
| 3,811,321 A | | 5/1974 | Urbanosky |
| 3,813,936 A | | 6/1974 | Urbanosky et al. |
| 3,859,851 A | | 1/1975 | Urbanosky |
| 4,941,345 A | * | 7/1990 | Altemark ................. G01N 9/32 73/23.2 |
| 4,994,671 A | | 2/1991 | Safinya et al. |
| 5,515,733 A | * | 5/1996 | Lynnworth ................. 73/861.27 |

(Continued)

OTHER PUBLICATIONS

Ball, et al., "Phase behavior and physical properties of petroleum reservoir fluids from acoustic measurements", Journal of Petroleum Science and Engineering, vol. 34, 2002, pp. 1-11.

(Continued)

*Primary Examiner* — Edward Cosimano
(74) *Attorney, Agent, or Firm* — Kenneth L. Kincaid

(57) ABSTRACT

Variable volume systems and methods of use thereof described herein are capable of making calibrated determinations of fluid properties and phase behavior of a fluid sample. The determinations can be calibrated based on one or more calibration functions, such as system volume corrected for pressure and temperature variations. Cross-checking the results of measurements can be used to determine accuracy of the calibration or monitor for leaks or other anomalies of the variable volume systems. The variable volume systems can be implemented in a well logging tool and are capable of being calibrated downhole.

19 Claims, 7 Drawing Sheets

(56) References Cited

U.S. PATENT DOCUMENTS

| | | | |
|---|---|---|---|
| 5,932,793 A | | 8/1999 | Dayton et al. |
| 6,065,328 A | * | 5/2000 | Dayton et al. ............... 73/25.01 |
| 6,209,387 B1 | * | 4/2001 | Savidge ....................... 73/24.05 |
| 6,474,152 B1 | * | 11/2002 | Mullins et al. ............ 73/152.22 |
| 6,640,625 B1 | | 11/2003 | Goodwin |
| 7,114,562 B2 | | 10/2006 | Fisseler et al. |
| 7,913,556 B2 | * | 3/2011 | Hsu ........................ E21B 49/10 |
| | | | 702/6 |
| 2003/0033866 A1 | | 2/2003 | Diakonov et al. |
| 2004/0026076 A1 | | 2/2004 | Goodwin et al. |
| 2006/0070426 A1 | | 4/2006 | Pelletier |
| 2007/0062695 A1 | | 3/2007 | Harrison et al. |
| 2007/0119244 A1 | * | 5/2007 | Goodwin et al. .......... 73/152.28 |
| 2008/0143330 A1 | * | 6/2008 | Madio et al. ................. 324/303 |
| 2008/0163680 A1 | * | 7/2008 | DiFoggio ................... 73/152.27 |
| 2009/0308600 A1 | * | 12/2009 | Hsu ........................ E21B 49/10 |
| | | | 166/250.01 |
| 2010/0012586 A1 | | 1/2010 | Angelescu et al. |
| 2013/0110401 A1 | * | 5/2013 | Hsu et al. ......................... 702/6 |
| 2013/0239671 A1 | * | 9/2013 | Gisolf ..................... E21B 47/10 |
| | | | 73/152.05 |

OTHER PUBLICATIONS

Benedetto, et al., "Speed of Sound in Pure Water at Temperatures between 274 and 394K and at Pressures up to 90 MPa1". International Journal of Thermophysics, vol. 26 (6), Nov. 2005, pp. 1667-1680.

Daridon, et al., "Experimental Measurements of the Speed of Sound in n-Hexane from 293 to 373 K and up to 150 MPa", International Journal of Thermophysics, vol. 19 (1), Jan. 1998, pp. 145-160.

Davis, et al., "Compression of Mercury at High Pressure", Journal of Chemical Physics, vol. 46, 1967, 11 pages.

Lago, et al., "A new method to calculate the thermodynamical properties of liquids from accurate speed-of-sound measurements", J. Chem. Thermodynamics, vol. 40, 2008, pp. 1558-1564.

Lago, et al., "A recursive equation method for the determination of density and heat capacity: Comparison between isentropic and isothermal integration paths", J. Chem. Thermodynamics, vol. 42, 2010, pp. 462-465.

Lago, et al., "Thermodynamic properties of acetone calculated from accurate experimental speed of sound measurements at low temperatures and high pressures", J. Chem Thermodynamics, vol. 41, 2009, pp. 506-512.

Lago, et al., "A novel application of Recursive Equation Method for determining thermodynamic properties of single phase fluids from density and speed-of-sound measurements", J. Chem. Thermodynamics, vol. 58, 2013, pp. 422-427.

Sun, et al., "Acoustic and Thermodynamic Properties of Benzene and Cyclohexane as a Function of Pressure and Temperature", Physics and Chemistry of Liquids: An International Journal, vol. 16 (3), 1987, pp. 163-178.

Sun, et al., "Determination of the thermodynamic properties of liquid ethanol from 193 to 263 K and up to 280 MPa from speed-of-sound measurements", International Journal of Thermophysics, vol. 12 (2), 1991, pp. 381-395.

Sun, et al., "Determination of the Thermodynamic Properties of Liquid Methanol from 203 to 263 K and up to 280 MPa from Speed of Sound Measurements", Reports of the Bunsen Society of Physical Chemistry, vol. 94 (4), Apr. 1990, pp. 528-534.

International Search Report and the Written Opinion for International Application No. PCT/US2013/023965 dated May 9, 2013.

* cited by examiner

DETERMINATION OF THERMODYNAMIC PROPERTIES OF A FLUID BASED ON DENSITY AND SOUND SPEED

BACKGROUND

Accurate measurement of fluid properties especially phase behavior is essential in a variety of fields, for example, in the oil and gas industries. In these industries, naturally occurring hydrocarbon fluids can include a wide range of phases, such as dry natural gas, wet gas, condensate, light oil, black oil, heavy oil, and heavy viscous tar. The physical properties of these various hydrocarbon fluids, such as density, viscosity, and compressibility can vary considerably. In addition, the separation of each of the hydrocarbon fluid compositions into distinctly separate gas, liquid and solid phases, each with its own physical properties, can occur at certain contours of pressure and temperature within the formation. This is referred to generally as the "phase behavior" of the hydrocarbon.

The economic value of a hydrocarbon reserve, the method of production, the efficiency of recovery, the design of production hardware systems, etc., all depend upon the physical properties and phase behavior of the reservoir hydrocarbon fluid. Hence, it is important that the fluid properties and phase behavior of the hydrocarbon be determined accurately following the discovery of the hydrocarbon reservoir, so that a decision of whether it is economically viable to develop the reservoir can be made; and if viable, an appropriate design and plan for the development of the reservoir can be adopted.

SUMMARY

The following presents a simplified summary of the innovation in order to provide a basic understanding of some aspects of the innovation. This summary is not an extensive overview of the innovation. It is not intended to identify key/critical elements of the innovation or to delineate the scope of the innovation. Its sole purpose is to present some concepts of the innovation in a simplified form as a prelude to the more detailed description that is presented later.

The innovation disclosed herein, in one aspect thereof, comprises a system that can be used to determine one or more thermodynamic properties of a fluid. The system can include a fluid sample container that alters a temperature or a pressure of a fluid sample, and an optical fluid analyzer (OFA) that determines a compressibility of the fluid sample at each of a plurality of pressures and temperatures. Additionally the system can include a sound speed component that measures a speed of sound in the fluid sample at each of the plurality of pressures and temperatures. The system can also comprise an analysis component that calculates, at each of the plurality of pressures and temperatures, a density of the fluid sample based at least in part on the compressibility and the speed of sound. The analysis component can determine one or more thermodynamic properties of the fluid sample based at least in part on the density and the speed of sound, wherein the one or more thermodynamic properties comprises at least one of a heat capacity of the fluid sample, an expansivity of the fluid sample, or an adiabatic index of the fluid sample.

In another aspect, the subject innovation can comprise a method capable of determining thermodynamic properties of a fluid. The method can include the steps of capturing a sample of a fluid and determining, for each of a plurality of pressures in a range of pressures, a density, a speed of sound, and a heat capacity of the sample. The determining step can comprise the steps of: measuring the speed of sound in the sample for each of a plurality of temperatures in a range of temperatures; calculating a density for the sample for each of the plurality of temperatures; and estimating the heat capacity for the sample for each of the plurality of temperatures. Additionally, the method can include the step of calculating one or more thermodynamic properties based at least in part on the determined density, speed of sound, and heat capacity, wherein the one or more thermodynamic properties comprise at least one of a heat capacity of the sample, an expansivity of the sample, or an adiabatic index of the sample.

To the accomplishment of the foregoing and related ends, certain illustrative aspects of the innovation are described herein in connection with the following description and the annexed drawings. These aspects are indicative, however, of but a few of the various ways in which the principles of the innovation can be employed and the subject innovation is intended to include all such aspects and their equivalents. Other advantages and novel features of the innovation will become apparent from the following detailed description of the innovation when considered in conjunction with the drawings.

DETAILED DESCRIPTION

Figure 1:
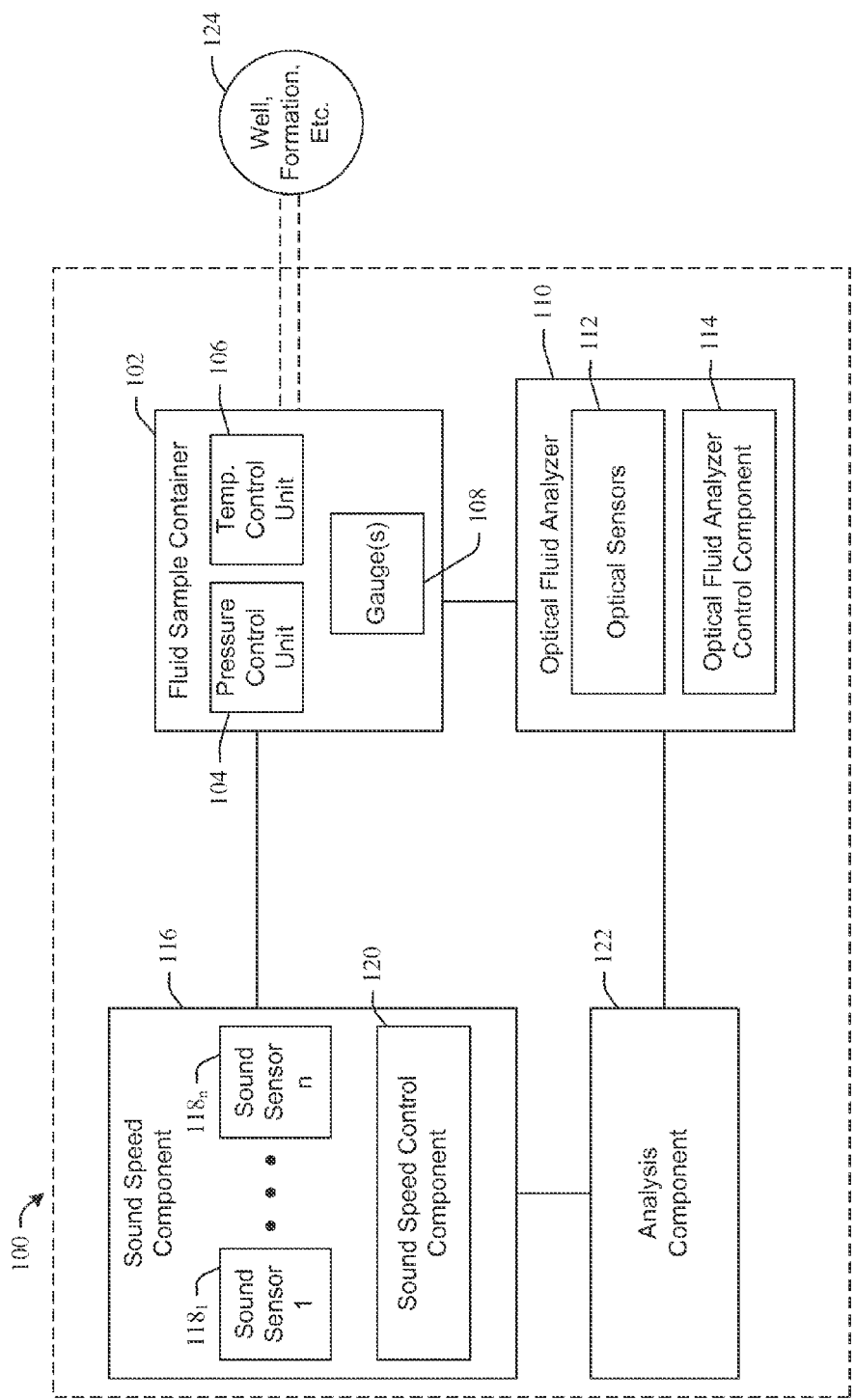
FIG. 1 illustrates an example system that is capable of determining one or more thermodynamic properties of a fluid sample in accordance with aspects of the subject innovation.

The innovation is now described with reference to the drawings, wherein like reference numerals are used to refer to like elements throughout. In the following description, for purposes of explanation, numerous specific details are set forth in order to provide a thorough understanding of the subject innovation. It may be evident, however, that the innovation can be practiced without these specific details. In other instances, well-known structures and devices are shown in block diagram form in order to facilitate describing the innovation.

As used in this application, the terms "component" and "system" are intended to include, at least in some cases, reference to a computer-related entity, either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution, and a component can be localized on one computer and/or distributed between two or more computers.

The subject innovation relates to the determination of any or all thermodynamic properties of a fluid based at least in part on measurements of the speed of sound (or sound speed) in the fluid. In the case of dense fluid or liquids, it is often relatively easy to measure pressure, density, and temperature (p, $\rho$, T), where $\rho$ is the density at moderate pressures. For example, vibrating-tube densimeters can be used. The subject innovation can include sound speed measurements in the regime where (p, $\rho$, T) are available to determine one or more thermodynamic properties of a fluid. As an example, systems and methods of the subject innovation can be used as an alternative to calorimetry in the determination of heat capacity, as discussed herein. The speed of sound, in combination with (p, $\rho$, T) data, can be the main source of experimental values of the heat-capacity ratio $\gamma$ and the isentropic compressibility $\kappa_S$ of pure liquids and mixtures. At higher pressures, (p, $\rho$, T) measurements can be much more difficult, even with vibrating tubes, and it is in this region that sound speed measurements in liquids can be of particular value. In such cases, the method or technique of analysis can involve numerical integration, as discussed further herein.

In various aspects, the subject innovation relates to determining all thermodynamic properties of the fluid (e.g., relative to petroleum applications, such as down-hole measurements of reservoir fluid, etc.) via the numerical integration of a combination of sound speed and density measurements performed over a temperature and pressure range. In aspects, density measurements can be determined as described in U.S. Pat. No. 6,640,625 to Goodwin, the entirety of which is incorporated herein by reference. Additionally, in some aspects, fluid compressibility (e.g., isothermal compressibility) can be measured utilizing an optical measurement method or apparatus, such as that of U.S. Pat. No. 6,474,152 to Mullins et al., the entirety of which is incorporated herein by reference, which can be implemented via an Optical Fluid Analyzer, such as that of U.S. Pat. No. 4,994,671 to Safinya et al., which provides a borehole apparatus that can include a testing chamber, means for directing a sample of fluid into the chamber, a light source preferably emitting near infrared rays and visible light, a spectral detector, a data base means, and a processing means, and the entirety of which is also incorporated herein by reference. Systems and methods of the subject innovation can be used in a wide variety of applications, including in the petroleum or natural gas industries, such as in connection with well logging, for example, in fluid analysis and sampling tools conveyed via a wireline or measurement while drilling (MWD) (or logging while drilling, LWD, which is intended to be included within MWD as used herein) apparatus.

The subject innovation can be used to investigate the properties of fluids in a variety of settings, including petroleum and natural gas well logging, such as production logging, or borehole investigative logging, such as in a MWD or wireline implementation as discussed herein.

Turning to FIG. 1, in one embodiment, the innovation includes a system 100 that is capable of determining one or more thermodynamic properties of a fluid sample in accordance with aspects of the subject innovation. These thermodynamic properties can include compressibility (e.g., isentropic, isothermal), specific heat capacity (e.g., isobaric, isochoric), heat capacity ratio, coefficient of thermal expansion, etc., including other thermodynamic properties that can be determined based on any combination of those and properties measurable by systems and methods of the subject innovation, which can include pressure, temperature, density, compressibility (e.g., isothermal), etc. System 100 is capable of determining these one or more thermodynamic properties of a fluid based at least in part on measurements of sound speed and density, optionally with estimates of molar isobaric specific heat capacity, although these are not required. These thermodynamic properties can be used to provide more accurate information regarding the behavior and properties of the fluid sample, and can be used to assess the composition or value of the fluid. In various embodiments, some or all of the components of system 100 can be integrated into a single tool or apparatus. In other embodiments, however, some of the components and associated functions (e.g., pressurizing or depressurizing a fluid sample (or, alternatively, altering the temperature of a fluid sample, etc.), taking measurements on the fluid sample, etc.) can be located and/or occur remotely (in whole or in part) from other components and associated functions (e.g., analysis, calibration, etc.). In various aspects, system 100 can be implemented in a well logging setting, such as in a wireline or MWD embodiment.

System 100 can include a fluid sample container 102 that can store at least a portion of fluid (e.g., from a well, etc.). Fluid sample container 102 can be substantially any container with a volume or pressure variation mechanism (e.g., at least one of a motor, moveable valve, etc., to at least one of pressurize or depressurize a fluid in fluid sample container 102). Examples of containers that can be used as fluid sample container 102 are laboratory sample containers, sample bottles, sample cells and other laboratory testing apparatuses, field testing equipment, etc., provided that there is an associated volume or pressure variation mechanism. In a petroleum setting, examples include sample containers or sample bottles used in a PVT (pressure, volume, and temperature) laboratory, containers or flow lines (or portions thereof) in well logging tools such as wireline tools or logging while drilling (LWD) tools, etc. System 100 can additionally comprise one or more components capable of altering the pressure and temperature of the fluid in fluid sample container 102. In some embodiments, these components can be included within fluid sample container 102. For example, in aspects, fluid sample container 102 can comprise a pressure control unit 104 that can pressurize or depressurize the fluid in fluid sample container 102, for example by having an expandable or contractable volume (e.g., via a moveable piston). In other aspects, fluid sample container 102 can comprise a temperature control unit 106 to alter the temperature (by substantially any means known in the art) of a fluid in fluid sample container 102, capable of providing a thermally controlled environment in fluid sample container 102. The pressure and temperature in fluid sample container 102 can be monitored via one or more gauges or sensors 108, which can allow for precision measurement and (via temperature and pressure control units 106 and 104) control of pressure and temperature. In an example operation, a valve of fluid sample container 102 can be opened and a fluid sample collected. The valve can be closed, and measurements can be conducted on the fluid sample. Additionally, the pressure and temperature of the fluid sample can be varied, and additional measurements can be conducted at a plurality of temperature and pressure values.

System 100 can further comprise an optical fluid analyzer (OFA) 110, such as explained in greater detail in the incorporated reference U.S. Pat. No. 4,994,671 to Safinya et al., capable of optically determining one or more properties (e.g., compressibility) of the fluid sample in fluid sample container 102. OFA 110 can comprise one or more optical sensors 112 capable of measuring compressibility, as set forth in greater detail in the incorporated U.S. Pat. No. 6,474,152 to Mullins et al. For each of a plurality of pressure and temperature values, the one or more optical sensors 112 of OFA 110 can make an optical measurement, which can include measurement of the absorption of light at one or more selected wavelengths, as described further herein. Based on these measurements, OFA control component 114 can determine a compressibility (e.g., isothermal compressibility) of the fluid sample.

The OFA 110 can determine the isothermal compressibility of the fluid sample by determining spectral absorption of the fluid sample at a plurality of pressures at a fixed temperature. For example, for a given fluid sample, the magnitude of the absorption will depend upon the pressure of the fluid; the higher the pressure, the greater the absorption. It has been experimentally determined that the change in the absorption that results from a change in pressure correlates directly with fluid compressibility. For example, for pure methane gas, the absorption peak in the 1640-1675 nm range (the "methane absorption peak") increases from an optical density of approximately 0.3 to an optical density of nearly 0.7 as pressure is increased from 2 kpsi to 20 kpsi. By integrating, the area under each of the optical density curves can be found. The optically determined peaks areas of a fluid (e.g., methane) at different temperature have a linear relationship with the mass density of the fluid (e.g., methane) at those temperatures. In another example, the optically determined peak areas of a methane/heptane hydrocarbon mixture have a linear relationship with the mass density of the mixture at different temperatures. It is to be understood that the slope of the line defining the linear relationship between peak areas and mass density is specific to the hydrocarbon fluid or fluid mixture being analyzed. Because of the linear relationship between the density $\rho$ and peak area $\psi$, it can be shown that the isothermal compressibility $$\kappa_T = \frac{1}{\psi}\left(\frac{\partial \psi}{\partial P}\right)_T,$$

where $\kappa_T$ is the compressibility, $\partial \psi$ is the differential of peak area, and $\partial P$ is the differential of pressure. This can be estimated as $$\kappa_T = \frac{1}{\psi}\left(\frac{\Delta \psi}{\Delta P}\right)_T,$$

where $\Delta \psi$ is the change in peak area above the initial peak area $\psi$, and $\Delta P$ is the change of pressure above the initial pressure.

It is to be noted that at any given temperature, fluid compressibility can be determined from the change in the peak area (due to the change in pressure) divided by the change in pressure, and the peak area itself. The change in pressure can be measured by a pressure gauge 108, while the change in peak area can be measured by the optical sensors 112. The peak area determination for a particular optical sensor 112 can be determined from the raw data count of the optical sensor 112. In other words, the peak area can be defined as the optical density for the wavelength width of that channel. Thus, optical sensors 112 at wavelengths corresponding to peak areas of fluids which are likely to be encountered can be utilized; for example, for hydrocarbons, wavelengths at or around 6,000 cm$^{-1}$ to 5,800 cm$^{-1}$ can be utilized (the absorption peaks of methane and crude oil respectively). These measurements can occur at two or more pressures to provide one or more estimates of compressibility (e.g., of which a mean or median can be selected if there are more than two estimates, etc.).

Additionally, system 100 can further comprise a sound speed component 116 capable of determining the speed of sound in the fluid sample. This speed of sound can be measured in any of a variety of ways, as described herein, which can give rise to multiple different embodiments of sound speed component 116. The sound speed can be determined, for example, by means of one or more of (1) determination of the time-of-flight between two piezoelectric elements, (2) a single-path time-of-flight measurement based on a pulse-echo measurement, (3) via an interferometric method, or (4) using a dual-path single transducer time-of-flight measurement. Depending on the specific way in which the speed of sound is to be determined, the actual sound sensors $118_1$-$118_n$ involved may vary, and may include one or more sound transducers, one or more reflectors, etc. Based on measurements recorded by the sound sensors $118_1$-$118_n$, a sound speed control component 120 can determine a speed of sound in the fluid sample. For example, in an arrangement using two sound transceivers (e.g., sonic, ultrasonic, etc.), a sound is transmitted from one to the other, and the transit time t1 of the sound can be recorded. Optionally, a sound may also be transmitted from the second transceiver to the first, with a second transit time t2 being recorded. These one or more transit times, taken in conjunction with the know distance between the transceivers, can yield a velocity for sound in the fluid sample.

Based on the determined compressibility of the fluid sample and the speed of sound through the fluid sample, the density can be calculated by analysis component 122 by applying analytical methods and techniques described further herein. It is to be appreciated that in some aspects, the density calculation can be performed using the isothermal compressibility obtained by the OFA 110, or in other aspects, the isentropic compressibility can be obtained from the isothermal compressibility using estimates of $c_p$ and $\alpha$. It is to be appreciated that the operation of OFA 110 and that of sound speed component 116 can be performed sequentially (in either order) or simultaneously.

The temperature can be varied in increments, and measurements repeated to determine values of sound speed and density along an isobar. From the speed of sound and the initial values on the isobar at $p=p_0$, it is possible to determine both $(\partial \rho/\partial p)_T$ and $(\partial c_p/\partial p)_T$, and hence to estimate $\rho$ and $c_p$ on a new isobar at $p_1=p_0+\delta p$ by means of first-order Taylor (or other, as explained herein) expansions. Repetition of the procedure (e.g., using the estimated values) can allow development of the solution isobar-by-isobar until an upper limit in pressure is reached. In some aspects, a second-order integration method can be used to increase the efficiency of the procedure. Based on the calculated density and the measured speed of sound and the techniques described herein, any or all of the thermodynamic properties of the fluid sample can be determined by analysis component 122.

System 100 can be implemented in a variety of settings to obtain data on the fluid properties or phase behavior of a fluid sample. System 100 can be used in a laboratory setting, such as a PVT laboratory, etc. Additionally, system 100 can be used for well logging (e.g., to make measurements or a record of measurements related to materials penetrated by a borehole, etc.), including measuring fluid properties and phase behavior in situ (e.g., in petroleum or natural gas applications, etc.). In well logging applications, various embodiments of system 100 can be used as wireline tools (e.g., by lowering the system or portions thereof into a borehole after drilling is completed, etc.). In other aspects related to well logging, some embodiments of system 100 can be used as a measurement while drilling (MWD) tools, logging while drilling (LWD) tools, or any other types of drill string downhole tools (e.g., by incorporating the system or portions thereof into a drill collar, other portions of the bottom hole assembly, etc.). In such well logging applications, system 100 can be connected to and obtain fluid samples from a borehole or well, formation, etc. 124.

In view of the aspects and features described, methodologies that may be implemented in accordance with embodiments of the subject innovation will be better appreciated with reference to the figures. While, for purposes of simplicity of explanation, the one or more methodologies shown herein, e.g., in the form of a flow chart, are shown and described as a series of acts, it is to be understood and appreciated that the subject innovation is not limited by the order of acts, as some acts may, in accordance with the innovation, occur in a different order and/or concurrently with other acts from that shown and described herein. For example, those skilled in the art will understand and appreciate that a methodology could alternatively be represented as a series of interrelated states or events, such as in a state diagram. Moreover, not all illustrated acts may be required to implement a methodology in accordance with the innovation.

Figure 2:
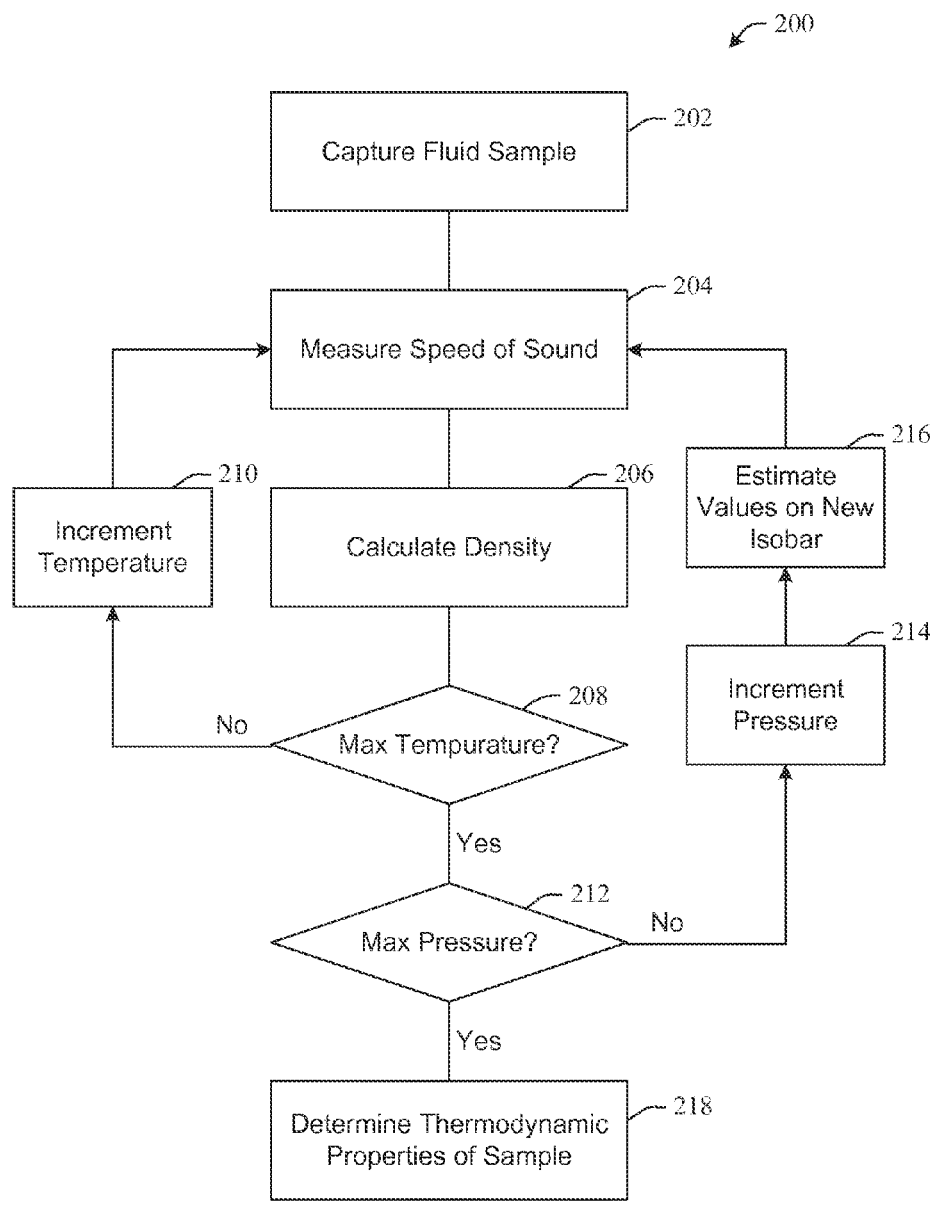
FIG. 2 shows a flowchart of an example method of determining one or more thermodynamic properties of a fluid sample in accordance with the subject innovation.

In various aspects, as illustrated in FIG. 2, the subject innovation can include a method 200 of determining thermodynamic properties of a fluid. The method can begin at step 202, wherein a sample of the fluid can be captured. This can be captured in substantially any vessel that can provide for altering the pressure and temperature of the sample, such as the fluid sample container described herein, etc. Next, at step 204, the speed of sound in the sample can be measured at a given temperature and pressure (which can be, for example, a corner of a selected rectangular (T, p) space, such as a lowest temperature and pressure, etc.), such as described herein in connection with the sound speed component. At step 206, the density of the sample can be calculated, for example, based on the sound speed and compressibility as explained herein, or calculated based on mass and volume in situations where such measurements can be made without unacceptable error. At step 208, a determination can be made whether a maximum temperature has been reached (e.g., a selected maximum, or based on equipment limitations, phase behavior, etc.). If a maximum temperature has not been reached, the method can proceed to step 210, incrementing (although only incrementing is discussed, it is intended to include decrementing as used herein, in which case the "maximum" temperature would be a corresponding minimum) the temperature while maintaining the pressure, before repeating step 204 and subsequent steps. If a maximum temperature has been reached, then at step 212, a determination can be made whether a maximum pressure has been reached (e.g., a selected maximum, or based on equipment limitations, phase behavior, etc.). If not, the method can proceed to step 214, incrementing the pressure (and potentially reducing the temperature, if it is to be incremented instead of decremented on the following steps). At step 216, based on analytical techniques and methods described herein, values for the new isobar (i.e., at the pressure selected in step 214) can be calculated, which can include estimating $\rho$ and $c_p$ (e.g., based on calculating both $(\partial \rho/\partial p)_T$ and $(\partial c_p/\partial p)_T$, etc., as described further herein). The procedure can then repeat at step 204, taking values at the new pressure in steps 204-210 for each temperature in the range of temperatures. Based on steps 204-216, the method can iterate over a plurality of isobars, and at each isobar, estimating the values needed for the method to continue at the next isobar. If a maximum pressure has been reached, then at step 218, based on the measured, calculated and estimated values per the analytical techniques and methods described herein, one or more thermodynamic properties of the sample can be determined, such as in the range of the rectangular (T, p) space, a subset thereof, extrapolated outside of that space, etc.

What follows is a more detailed discussion of systems, methods, and apparatuses associated with specific embodiments and aspects of the subject innovation. To aid in the understanding of aspects of the subject innovation, theoretical analysis and experimental results associated with specific experiments that were conducted are discussed herein. However, although for the purposes of obtaining the results discussed herein, specific choices were made as to the selection of various aspects of the theoretical models and—such as selection of mathematical forms or analysis techniques for various systems and methods discussed herein (e.g., polynomial solutions forms, use of $\chi^2$ measure, etc.), design and application of device (e.g., petroleum well logging, etc.), the setting in which the device is employed (e.g., as a wireline tool, a logging while drilling tool, etc.), as well as other aspects—the systems and methods described herein can be employed in other contexts, as well. For example, aspects of the subject innovation can be utilized to determine thermodynamic properties of a fluid sample, independent of the ultimate application of those devices. In another example, systems discussed herein could be constructed with different choices of sensor elements than those discussed herein, and may have differing configurations, as explained in greater detail herein.

Techniques of the subject innovation can use determinations of the speed of sound and density of a fluid over a pressure and temperature region to determine various thermodynamic properties of the fluid.

For homogeneous fluid phases, which usually support only a single longitudinal sound mode, the propagation speed u is given by equation (1):

$$u^2(T, p) = \left(\frac{\partial p}{\partial \rho}\right)_S = (\rho \kappa_S)^{-1} = \gamma (\rho \kappa_T)^{-1}. \tag{1}$$

In equation (1), p is pressure, $\rho$ is mass density, S is entropy, $\kappa_S$ is the isentropic (i.e., at constant entropy) compressibility, defined by equation (2):

$$\kappa_S = -\frac{1}{V}\left(\frac{\partial V}{\partial p}\right)_S = \frac{1}{\rho u^2}, \tag{2}$$

$\kappa_T$ is the isothermal (i.e., at constant temperature) compressibility, defined by equation (3):

$$\kappa_T = -\frac{1}{V}\left(\frac{\partial V}{\partial p}\right)_T = -\left(\frac{\partial \ln V}{\partial p}\right)_T = \rho^{-1}\left(\frac{\partial \rho}{\partial p}\right)_T = \rho^{-1}\left(u^{-2} + \frac{T\alpha^2}{c_p}\right), \quad (3)$$

and $\gamma = c_p/c_V$, where $c_p$ and $c_V$ are, respectively, the molar isobaric (i.e., at constant pressure) and isochoric (i.e., at constant volume) specific heat capacities (and $\gamma$ is the heat capacity ratio or adiabatic index). $\kappa_S$ and $\kappa_T$ are interrelated by equation (4):

$$\kappa_T - \kappa_S = \frac{T\alpha^2 V}{C_p}, \quad (4)$$

where $\alpha$ is the isobaric expansivity or coefficient of thermal expansion defined by equation (5):

$$\alpha = \frac{1}{V}\left(\frac{\partial V}{\partial T}\right)_p = \left(\frac{\partial \ln V}{\partial T}\right)_p = \rho^{-1}\left(\frac{\partial \rho}{\partial T}\right)_p. \quad (5)$$

In the event that independent means of measuring $\kappa_S$, $\kappa_T$, $\alpha$, T, V and $C_p$ of a phase are available, then equation (4) can be used to test the measurements for thermodynamic consistency.

Equation (1) is strictly valid only in the limits of vanishing amplitude and vanishing frequency of the sound wave, which may or may not be the case in practice, but it remains a useful approximation in many other situations. The situation corresponding to the first of these limits (vanishing amplitude) is easy to realize in practice, particularly in the petroleum industry (e.g., oil field services, etc.) where the ambient pressure is orders of magnitude greater than 0.1 MPa. Situations corresponding to the second limit (vanishing frequency) are often, but not always, realized; in practice, fluid densities on the order of 100 kg·m$^{-3}$, which are frequently experienced in oil fields, mean this requirement is usually met, owing to the presence of a relatively short mean-free path.

Equation (1) shows that the isentropic compressibility may be obtained from measurements of the speed of sound and the density, and that the isothermal compressibility may also be obtained if $\gamma$ is known (or vice versa). Equation (1) forms the basis of almost all experimental determinations of the isentropic compressibility. Since density and isothermal compressibility may be measured more-or-less directly and often without great difficulty, Equation (1) provides a convenient route to determine $\gamma$. In order to develop further the working equations between u and the equation of state of the medium, it is often convenient to work with (T, p) and massic (or specific) quantities, resulting in equation (6):

$$u^2 = \left[\left(\frac{\partial \rho}{\partial p}\right)_T - \frac{T}{\rho^2 c_p}\left(\frac{\partial \rho}{\partial T}\right)_p^2\right]^{-1}, \quad (6)$$

and equation (7):

$$\left(\frac{\partial c_p}{\partial p}\right)_T = -T\left(\frac{\partial^2 v}{\partial T^2}\right)_p, \quad (7)$$

where $v = \rho^{-1}$ is the specific volume. The method can be applied in any of a variety of (T, p) spaces, for example, in a rectangular (T, p) space with initial values of $\rho$ and $c_p$ specified (or determined) along the isobar at the lowest pressure $p_0$ (e.g., 0.1 MPa, or some other suitable value). If the initial values of density are sufficiently accurate, both the first and second temperature derivatives can be determined; alternatively, a separate determination of thermal expansion can be made. From the speed of sound and the initial values on the isobar at $p=p_0$, it is possible to determine both $(\partial \rho/\partial p)_T$ and $(\partial c_p/\partial p)_T$ and hence to estimate $\rho$ and $c_p$ on a new isobar (e.g., at $p_1 = p_0 + \delta p$, by means of first-order Taylor expansions, although other approximations, such as higher order Taylor expansions, etc. can be used alternatively). Repetition or iteration of the procedure (e.g., using the estimated values) can allow development of the solution isobar-by-isobar until the upper limit in pressure is reached. In some aspects, a second-order integration method can be used to increase the efficiency of the procedure.

The criteria for placement of the initial conditions require a path that cuts all isentropes in the solution region. For liquids, $(\partial p/\partial T)_S$ is much greater than in a gas and the isentropes rise steeply from the vapour pressure curve on a (p, T) diagram. Consequently, the isobar at the lowest pressure comes very close to meeting the criterion of cutting all isentropes that pass through the solution region. However, it does not fully satisfy that criterion because some additional isentropes flow in through the isotherm defining the low-temperature boundary of the integration domain, which may be the cause of error in application of the method. In aspects, one or more functions of temperature (e.g., polynomial, etc.) can be used to represent $\rho$ and $c_p$ on each isobar, and the usually slow variation of those quantities may help to stabilize the method despite the incomplete imposition of boundary conditions.

The integration discussed above requires as input u(p, T) and $\rho$(p, T) and can be used to obtain estimates of $c_p$ along with the boundary conditions that can be used in the recursive scheme to determine the thermodynamic properties by regression. Further, the method can provide a means of determining the isentropic compressibility of equation (2), the isobaric expansivity of equation (5), the isothermal compressibility from equation (3), and $C_V$ from equation (8):

$$c_V - c_p = -\rho^{-1}\left(\frac{T\alpha^2}{\kappa_T}\right). \quad (8)$$

In various aspects, the systems and methods of the subject innovation can omit the requirement to provide external estimates of $c_p$ at the reference conditions and can use the techniques described above to provide the initial estimate that can then be iterated to minimize a measure of error (such as the $\chi_2$ or some other measure of error).

Equation 6 can be recast as equation (9):

$$\left(\frac{\partial \rho}{\partial p}\right)_T = \frac{T}{c_p \rho^2}\left(\frac{\partial \rho}{\partial T}\right)_p^2 + u^{-2}, \quad (9)$$

and it can be shown that, as in equation (10):

$$\left(\frac{\partial c_p}{\partial \rho}\right)_T = -\frac{T}{\rho}\left[\frac{2}{\rho^2}\left(\frac{\partial \rho}{\partial T}\right)_p^2 - \rho^{-1}\left(\frac{\partial^2 \rho}{\partial T^2}\right)_p\right], \quad (10)$$

and equation (11):

$$c_p = \left[T\rho^{-2}\left(\frac{\partial \rho}{\partial T}\right)_p^2\right]\left[\left(\frac{\partial \rho}{\partial p}\right)_T - u^{-2}\right]^{-1}. \quad (11)$$

In embodiments of the subject innovation, the mathematical form of the solution can be established. In some aspects, polynomials can be used for the mathematical form, for example, polynomials of the form shown in equations (12), (13), and (14), or some other approximation function:

$$u(p, T) = \sum_i^{i=N}\sum_j^{j=M} a_{i,j}(p - p_{ref})^i(T - T_{ref})^j \quad (12)$$

$$\rho(p, T) = \sum_i^{i=N}\sum_j^{j=M} b_{i,j}(p - p_{ref})^i(T - T_{ref})^j. \quad (13)$$

$$c_p(p, T) = \sum_i^{i=N}\sum_j^{j=M} c_{i,j}(p - p_{ref})^i(T - T_{ref})^j. \quad (14)$$

Next, these equations can be solved recursively for the coefficients a, b, and c. Additionally, initial conditions at the reference pressure $p_{ref}$ can further be provided, which can be of the same form as the mathematical form established for the solution. In aspects utilizing the form of equations (12), (13), and (14), the form of initial conditions can be as in equations (15) and (16), although it is to be understood that with a different selection of mathematical form of the solution, the form of the initial conditions will vary accordingly:

$$\rho(p_{ref}, T) = \sum_i^{i=N}\sum_j^{j=M} b_{i,j}(T - T_{ref})^j \quad (15)$$

$$c_p(p_{ref}, T) = \sum_i^{i=N}\sum_j^{j=N} c_{i,j}(T - T_{ref})^j \quad (16)$$

The $c_p(p_{ref}, T_{ref})$ can be determined from equation (11), where the term $(\partial \rho/\partial T)_p$ can be obtained from equation (15) as shown in equation (17):

$$\left(\frac{\partial \rho}{\partial T}\right)_p = \sum_{j=}^{M} jb_{0,j}(T - T_{ref})^{j-1} \quad (17)$$

and for $(\partial \rho/\partial p)_T$ as in equation (18):

$$\left(\frac{\partial \rho}{\partial p}\right)_T = \sum_{i=1}^{N} ib_{i,0}(T - T_{ref})^{i-1}. \quad (18)$$

The u can be known from equation (12). At the reference temperature and pressure, $c_p$ can then be given by $$c_p(p_{ref}, T_{ref}) = \left(\frac{T_{ref}b_{0,1}^2}{b_{0,0}}\right)(b_{1,0} - a_{0,0}^{-2}), \quad (19)$$

which can be used as a first estimate to estimate equation (16).

Equations (12) through (14), which can be used to obtain $c_p(p, T)$ from a combination of $\rho(p, T)$ and $u(p, T)$ measurements, can be replaced by polynomials with rational exponent of ratios to give equations (20), (21), and (22):

$$u(p, T) = \sum_i^{i=N}\sum_j^{j=M} a_{i,j}(p/p_{ref})^{i/\alpha}(T/T_{ref})^{j/\beta}, \quad (20)$$

$$\rho(p, T) = \sum_i^{i=N}\sum_j^{j=M} b_{i,j}(p/p_{ref})^{i/\alpha}(T/T_{ref})^{j/\beta}, \quad (21)$$

and $$c_p(p, T) = \sum_i^{i=N}\sum_j^{j=M} c_{i,j}(p/p_{ref})^{i/\alpha}(T/T_{ref})^{j/\beta}. \quad (22)$$

In equations (20) through (22), $\alpha$ and $\beta$ are parameters that can be adjusted to minimize the difference between measured $\rho(p, T)$ and $u(p, T)$ and the respective calculated values. It has been shown that $\alpha \approx N$ and $\beta \approx M$ and typically $\alpha=3$ and $\beta=4$, although the $\alpha$ and $\beta$ are not critical.

In various aspects of the subject innovation, equations (20), (21) and (22) can be used rather than equations (12) through (14), which can result in a reduction in the number of adjustable parameters. Regardless of which equations are used, regression analysis can be used to determine the parameters (e.g., the parameters can be regressed to minimize the $\chi^2$ or some other measure of error of the sound speed and density data in continuous functions).

The implementation of the methodology expressed above depends on determining the speed of sound and density of the fluid in a schema that permits variations of pressure and temperature. The former can be achieved by varying the volume of a fixed amount of substance with a positive displacement pump (e.g., of the form provided by IFA). The temperature variation can be accomplished via a thermally controlled environment for both the $u(p, T)$ and $\rho(p, T)$ measurements. The pressure decrement can be selected based on limits imposed by the phase border pressure, while the temperature increment can depend on the limits imposed by the upper operating temperature of the conveyance system. For example, for a reservoir with a pressure of 100 MPa and temperature of 423 K containing a fluid for which the phase border occurs at a pressure of 35 MPa at T=423 K will result in a maximum pressure variation of 65 MPa and a temperature increase of 50 K. In applying the method, the measured data can be interpolated with the functions of the mathematical form selected (e.g., polynomial, etc.) to obtain the regularization data grid. In some aspects, to obtain representative heat capacity estimates, the input data to T and p can be extrapolated outside of the range of measurement, which can decrease the uncertainty of the $c_p$ so obtained near the boundary of the integration.

Sound speed measurements at high pressure can be performed using one or more of the following embodiments of sound speed measurement components: (1) determination of the time-of-flight between two piezoelectric elements, (2) a single-path time-of-flight measurement based on a pulse-echo measurement, (3) via an interferometric method, or (4) using a dual-path single transducer time-of-flight measurement. Embodiments comprising any of (1), (2), (3), and (4) are each based on a determination of the distance between the transducers or transducers and reflectors that can be achieved mechanically or from measurements with a fluid for which the speed of sound is known. For component type (4), a single piezoelectric transducer, which is used as both the source and detector of ultrasonic pulses, can be placed between two plane parallel reflectors such that, when energised with a suitable tone burst, sound pulses (e.g., ultrasonic, sonic, etc.) can be emitted from both surfaces. These pulses travel to the corresponding reflector and then return to the transducer, which, now operating as a receiver, detects their arrival. In principle, this approach can eliminate systematic errors arising from both instrumental and reflector effects. Example mechanical dimensions for component type (4) are a length of about 100 mm and a diameter of about 30 mm.

Experiments conducted in connection with the subject innovation were conducted involving water. These experiments showed that sound speed measurements with an uncertainty of ±0.1%, when combined with density data with an uncertainty of ±0.01% and the algorithm described above, can yield estimates of heat capacity with an uncertainty of about ±1%. For some applications, such as downhole well measurements, measurement uncertainty may be lower, which could give rise to greater error. To illustrate the effect on heat capacity consider sound speed measurements with an uncertainty of ±0.5% combined with density data with an uncertainty of ±0.1% yields heat capacity with an uncertainty of about ±6%.

Figure 3:
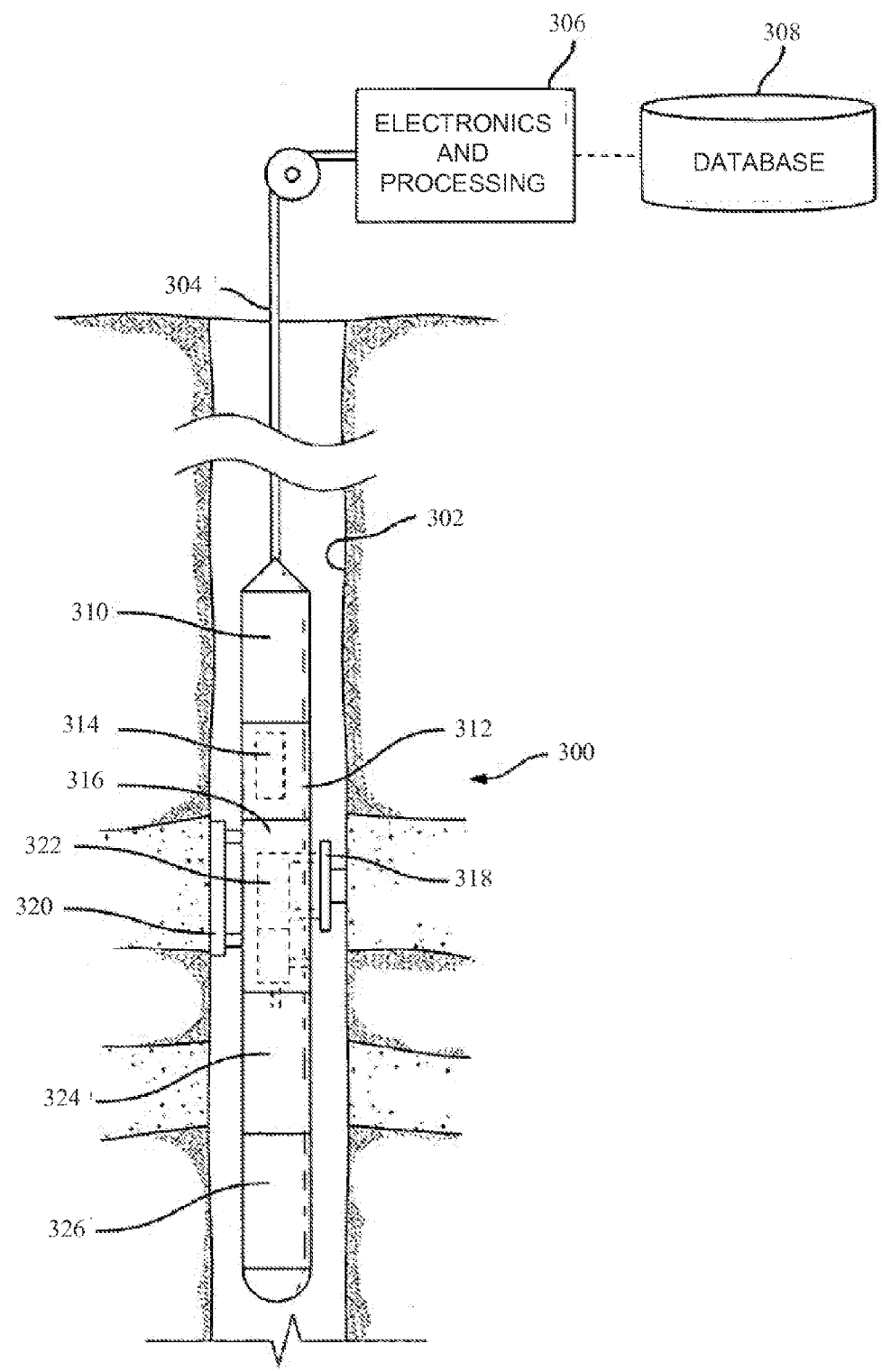
FIG. 3 illustrates an example wireline tool that may be used in connection with systems and methods of the subject innovation.

FIG. 3 depicts an example wireline tool 300 that may be used to extract and analyze formation fluid samples in accordance with the example methods and apparatus described herein. As shown in FIG. 3, the example wireline tool 300 can be suspended in a borehole (the terms "borehole" and "borehole tool," as used herein, are intended to encompass a well (e.g., cased, etc.) and a tool used in a well, as well as in a borehole) or wellbore 302 from the lower end of a multiconductor cable 304 that can be spooled to a winch (not shown) at the surface. At the surface, the cable 304 can be communicatively coupled to an electronics and processing system 306. The electronics and processing system 306 may include or be communicatively coupled to a database 308 that may be used to store measured or calculated values (e.g., thermodynamic values of fluids, such as for comparison with values determined in accordance with the subject innovation, which could be further used to identify one or more likely candidates among known fluids for the fluid sample, etc.) in accordance with systems and methods in aspects of the subject innovation. The wireline tool 300 can include an elongated body 310 that can include a collar 312 having a downhole control system 314 configured to control extraction of formation fluid from a formation 124, perform measurements on the extracted fluid, and to control systems or implement methods described herein to determine measurements on fluids based at least in part on calibrated system parameters.

The example wireline tool 300 can also include a formation tester 316 having a selectively extendable fluid admitting assembly 318 and a selectively extendable tool anchoring member 320 that can be respectively arranged on opposite sides of the elongated body 310. The fluid admitting assembly 318 can be configured to selectively seal off or isolate selected portions of the wall of the wellbore 302 to fluidly couple to the adjacent formation 124 and draw fluid samples from the formation 124. The formation tester 316 can also include a fluid analysis module 322 through which the obtained fluid samples can flow. The sample fluid may thereafter be expelled through a port (not shown) or it may be sent to one or more fluid collecting chambers 324 and 326, which may receive and retain the formation fluid samples for subsequent testing at the surface or a testing facility.

In the illustrated example, the electronics and processing system 306 and/or the downhole control system 314 are configured to control the fluid admitting assembly 318 to extract fluid samples from the formation 124 and to control the fluid analysis module 322 to measure the fluid samples. In some example implementations, the fluid analysis module 322 may be configured to analyze the measurement data of the fluid samples as described herein, such as based at least in part on one or more calibrated system parameters. In other example implementations, the fluid analysis module 322 may be configured to generate and store the measurement data and subsequently communicate the measurement data to the surface for analysis at the surface. Although the downhole control system 314 is shown as being implemented separate from the formation tester 316, in some example implementations, the downhole control system 314 may be implemented in the formation tester 316.

As described in greater detail below, the example wireline tool 300 may be used in conjunction with the example methods and apparatus described herein to obtain measurements related to phase behavior and fluid properties based at least in part on one or more calibrated system parameters. For example, the formation tester 316 may include one or more sensors, fluid analyzers and/or fluid measurement units disposed adjacent a flow line and may be controlled by one or both of the downhole control system 314 and the electronics and processing system 306 to determine the phase behavior, fluid properties, or other characteristics of fluid samples extracted from, for example, the formation 124. More specifically, the example wireline tool 300 can be configured to extract fluid samples from the formation 124 and to determine thermodynamic properties of those fluid samples. Further, the example wireline tool 300 can be configured to perform in situ determination of thermodynamic properties based at least in part on analytical methods and techniques discussed herein.

Figure 7:
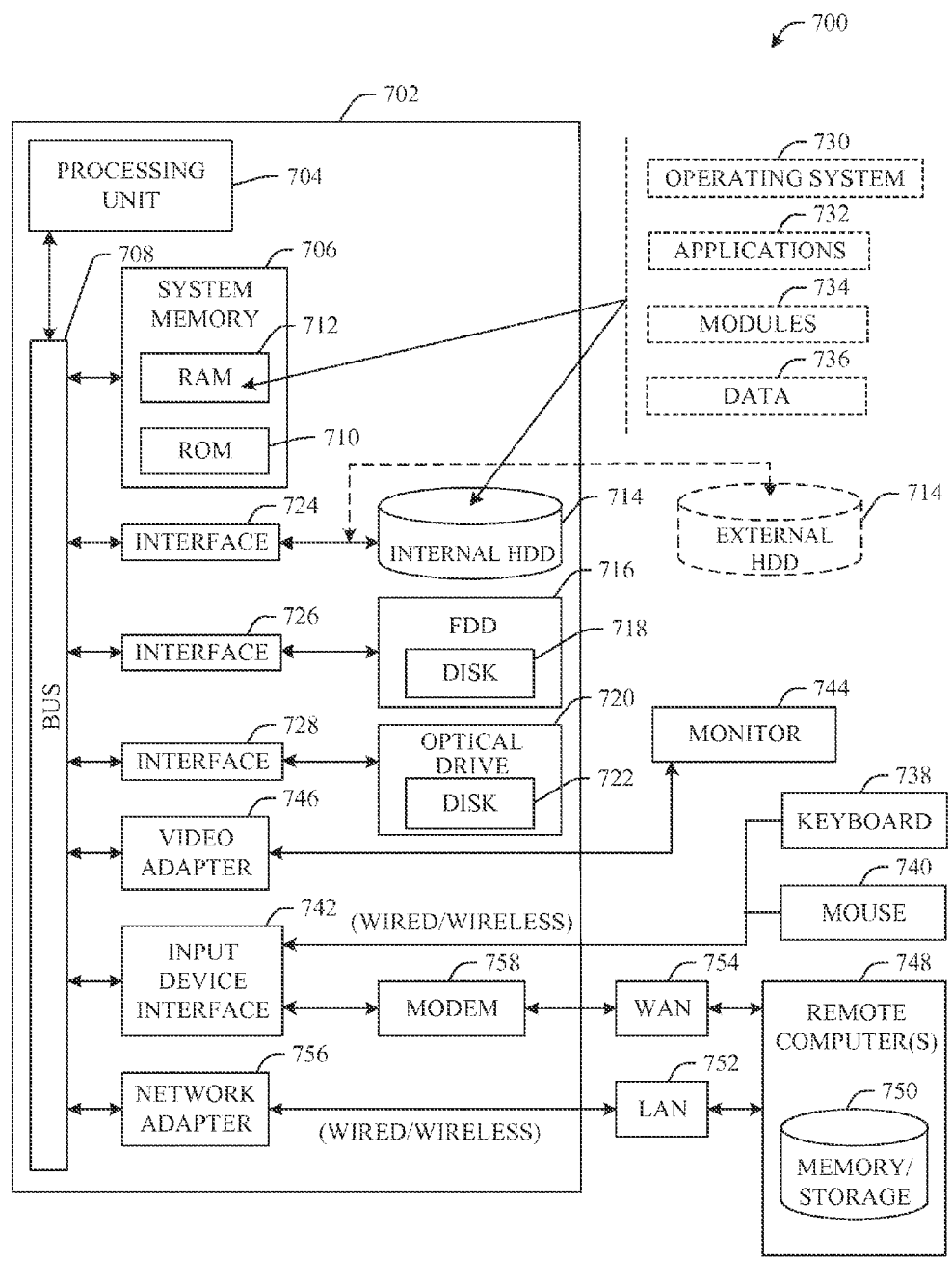
FIG. 7 illustrates a block diagram of a computer operable to execute in conjunction with aspects of the disclosed architecture.

The data processing associated with the example methods described herein may be performed by a processing unit or computer (e.g., as shown in FIG. 7) in the formation tester 316 and/or within the fluid analysis module 322, the downhole control system 314, the electronics and processing system 306, and/or within any other processing unit local or remote relative to the wireline tool 300.

Additional details of example methods and apparatuses for obtaining formation fluid samples may be had by reference to U.S. Pat. No. 3,859,851 to Urbanosky, U.S. Pat. No. 3,813,936 to Urbanosky, and U.S. Pat. No. 3,811,321 to Urbanosky, the entireties of which are hereby incorporated by reference herein. It should be appreciated, however, that the subject innovation need not be limited to these or other specific examples of methods or apparatuses for obtaining the formation fluids.

Figure 4:
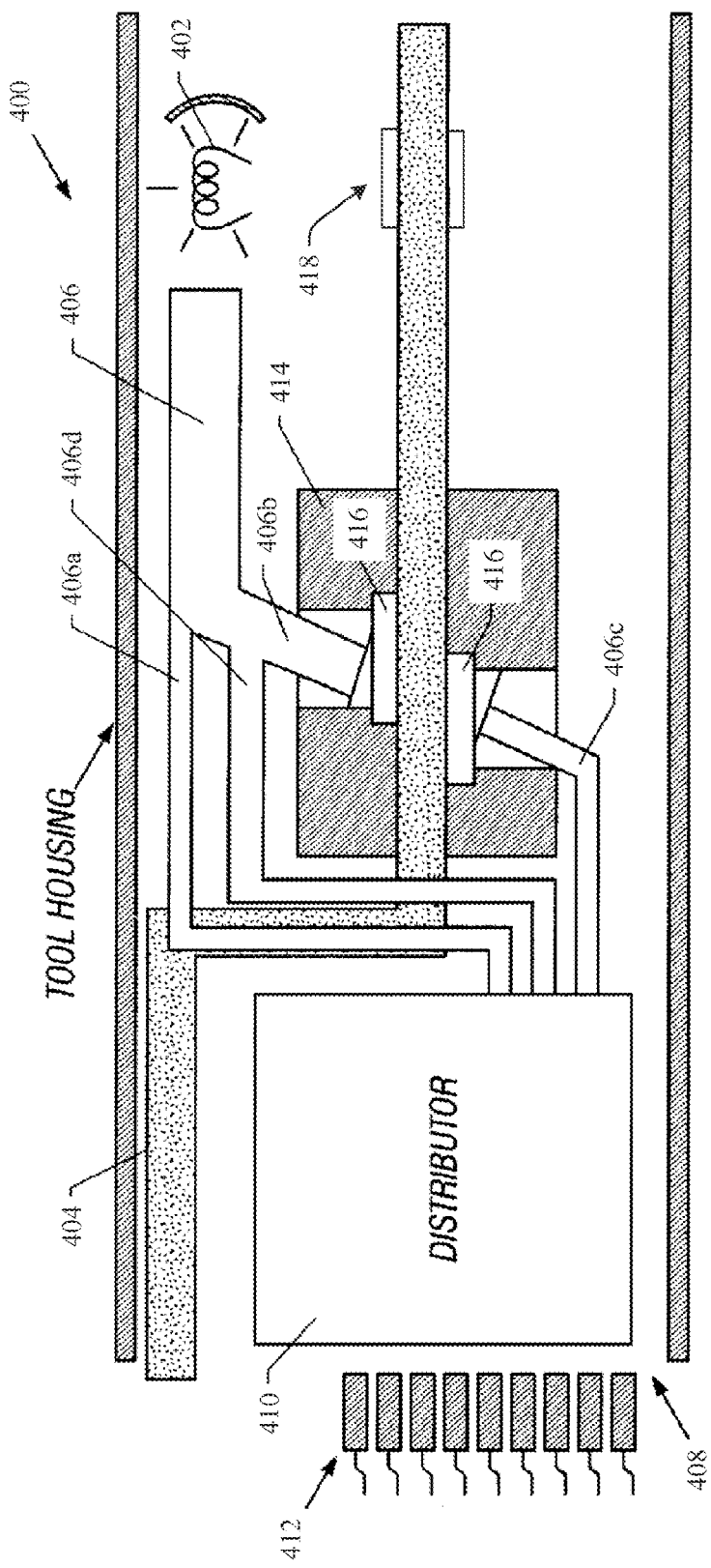
FIG. 4 shows a schematic diagram of an example apparatus capable of determining fluid compressibility and speed of sound in a fluid.

Turning now to FIG. 4, an example fluid analysis module 400 can include a light source 402, a fluid sample tube 404 (coupled to the fluid admitting assembly 318 of FIG. 3), fiber optic bundle 406, and a filter spectrograph 408 which can include a fiber coupler or distributor 410 and an associated detector array 412. The light source 402 can be any of a variety of light sources (e.g., light emitting diode, fluorescent, incandescent, etc., for example, an incandescent tungsten-halogen lamp) and can be kept at or near atmospheric pressure. The light source 402 can be relatively bright throughout a wavelength range, such as one selected based on the anticipated properties of one or more fluids the module 400 is intended to be used with (e.g., the incandescent tungsten-halogen lamp can have a near infrared wavelength region of 1 to 2.5 microns and down to approximately 0.5 microns, and acceptable emissions from 0.35 to 0.5 microns. Light rays from the light source 402 can be transported from the source to the fluid sample by at least part of fiber optic bundle 406. In aspects, the fiber optic bundle 406 can be split into various sections. A first small section 406a can go directly from the light source 402 to the distributor 410 and can be used to sample the light source. A second section 406b can be directed into an optical cell 414 through which the sample tube 404 can run and that can be used to illuminate the fluid sample. A third bundle 406c can collect light transmitted or scattered through the fluid sample and can provide the filter spectrograph 408 with the light for determining the absorption spectrum of the fluid sample. Optionally, a fourth fiber optic bundle 406d can collect light substantially backscattered from the sample for spectrographic analysis. The backscattered spectrum can be used in a variety of settings, such as if multiple phases are present simultaneously. A multi-position solenoid (e.g., three position), not shown, can be used to select which fiber optic bundle (e.g., of 406, 406a-406d) can be directed toward the filter spectrograph 408. In some aspects, a light chopper (not shown) can be included to modulate the light directed at the spectrograph at a frequency (e.g., 500 Hz, etc.) selected to avoid low frequency noise in the detectors.

As mentioned above, optical bundle 406b can direct the light towards the fluid sample. The fluid sample can be obtained from the formation by the fluid admitting assembly 318 and can be sent to the fluid analysis section 400 in fluid sample tube 404. The sample tube 404 can be a channel (e.g., rectangular or other shape; in one embodiment, two by six millimeter, although it can be smaller or larger, etc.) that can include a window section 416 (e.g., with windows made of sapphire, etc.) transparent to at least a portion of the spectrum of the light source 402. This window section 416 can be located in the optical cell 414 where the light rays can be arranged to illuminate the sample. In one example, sapphire can be chosen for the windows because it is substantially transparent to the spectrum of some example light sources provided herein and because it is highly resistant to abrasion. As indicated schematically in FIG. 4, in aspects, the window areas 416 may be relatively thick compared to the rest of the tube 404 to withstand high internal pressure. The fiber optic bundles 406b and 406c can be non-perpendicular to the window areas 416 so as to avoid specular reflection. Additionally, in aspects, the window areas can be slightly offset, as shown in FIG. 4, to keep them centered in the path of the transmitted light. The signals from the detectors can be digitized, multiplexed, and transmitted uphole via the cable 304 to the processing electronics 306 shown in FIG. 3. A sound speed component 418 can be included and can be mounted adjacent the tube 404 either upstream or downstream of the optical cell 414. The sound speed component 418 can be controlled by the uphole electronics 306 via the cable 304 shown in FIG. 3. In some embodiments, a pair of sound (e.g., sonic, ultrasonic, etc.) transceivers (e.g., quartz transducers, etc.) can be used, and can generate sound pulses for a duration in a frequency range (e.g., in the range of ten microseconds to one millisecond with a frequency in the range of 100 KHz to one MHz). In other embodiments, other methods of determining sound speed can be used (e.g., other than a pair of transceivers), and can include a single-path time-of-flight measurement based on a pulse-echo measurement, determination via an interferometric method, or determination using a dual-path single transducer time-of-flight measurement.

Figure 5:
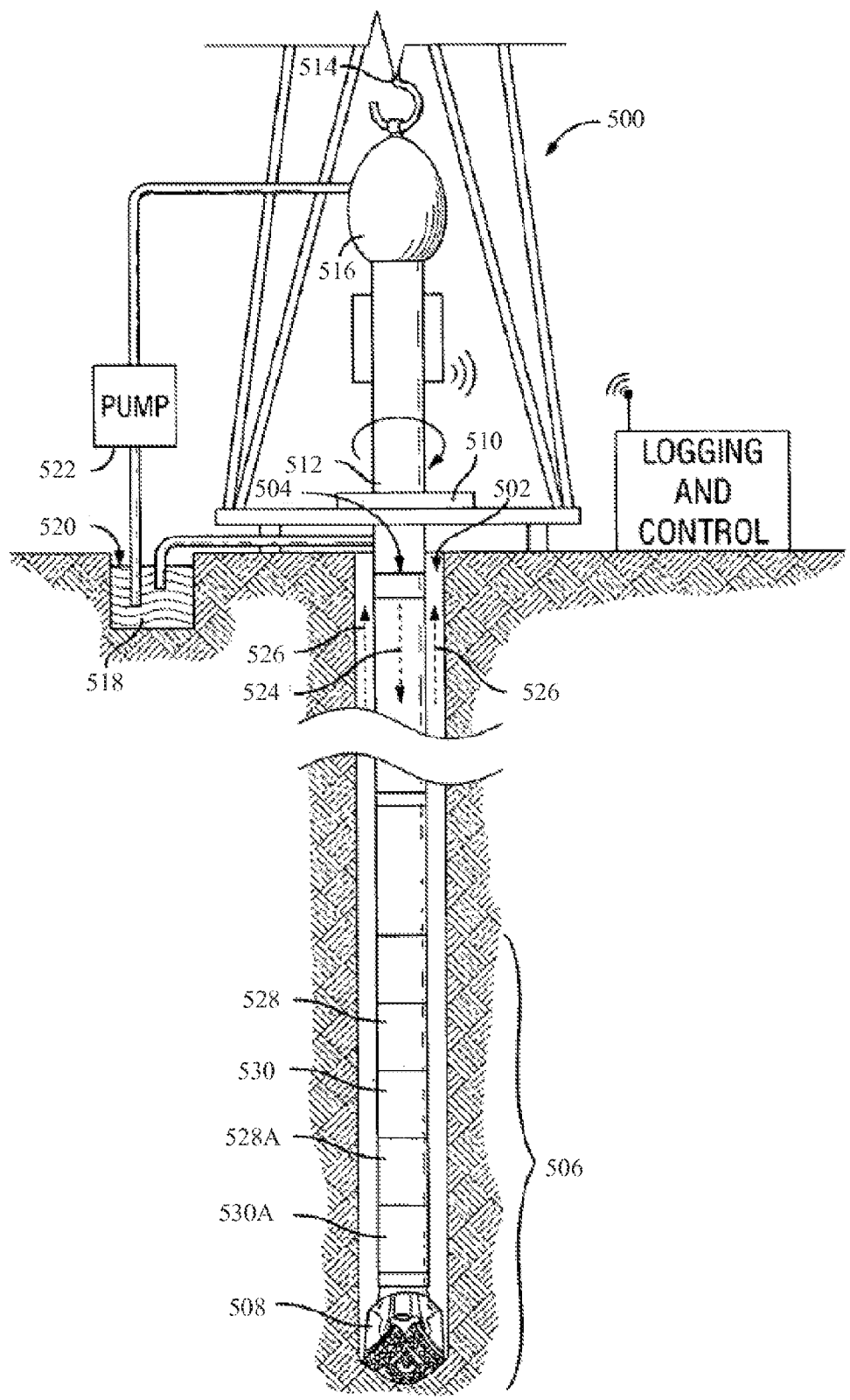
FIG. 5 illustrates an example while-drilling tool that may be used in connection with systems and methods of the subject innovation.

FIG. 5 illustrates a wellsite system in which one or more aspects of the subject disclosure may be employed. The wellsite and associated assembly 500 can be onshore or offshore. In the example system of FIG. 5, a borehole 502 is formed in subsurface formations by rotary drilling in a manner that would be well understood by a person of skill in the art in light of the subject disclosure. Embodiments of the subject disclosure can also use directional drilling.

A drill string 504 can be suspended within the borehole 502 and can have a bottom hole assembly 506 which can include a drill bit 508 at its lower end. The surface system can include platform and derrick assembly 500 positioned over the borehole 502, and assembly 500 can include a rotary table 510, kelly 512, hook 514 and rotary swivel 516. The drill string 504 can be rotated by the rotary table 510, energized by means not shown, which can engage the kelly 512 at the upper end of the drill string. The drill string 504 can be suspended from a hook 514, attached to a traveling block (also not shown), through the kelly 512 and a rotary swivel 516 which permits rotation of the drill string relative to the hook. As is to be understood, a top drive system could alternatively be used.

In the example of this embodiment, the surface system can further include drilling fluid or mud 518 stored in a pit 520 formed at the well site. A pump 522 can deliver the drilling fluid 518 to the interior of the drill string 504 via a port in the swivel 516, causing the drilling fluid to flow downwardly through the drill string 504 as indicated by the directional arrow 524. The drilling fluid can exit the drill string 504 via ports in the drill bit 508, and then can circulate upwardly through the annulus region between the outside of the drill string and the wall of the borehole, as indicated by the directional arrows 526. In this manner, the drilling fluid can lubricate the drill bit 508 and can carry formation cuttings up to the surface as it is returned to the pit 520 for recirculation.

The bottom hole assembly 506 of the illustrated embodiment can comprise a logging-while-drilling (LWD) module 528, a measuring-while-drilling (MWD) module 530, a roto-steerable system and motor, and the drill bit 508. The LWD module 528 and/or the MWD module 530 may be or comprise a tool that may be used to extract and analyze formation fluid samples in accordance with the example methods and systems described herein, such as that described in connection with FIG. 1 or 2. For example, the LWD module 528 and/or the MWD module 530 may include a system such as system 100 or the system of method 200. The LWD module 528 and/or the MWD module 530 may further comprise a downhole control system and/or otherwise be configured to control extraction of formation fluid from a formation 124, perform measurements on the extracted fluid, and to control the systems or implement the methods described herein to calibrate one or more system parameters, to perform cross-validation, or both.

The LWD module 528 can be housed in a special type of drill collar, as would be understood by a person of skill in the art in light of the subject disclosure, and can contain one or a plurality of known types of logging tools. It will also be understood that more than one LWD and/or MWD module can be employed, e.g. as represented at 528A and 530A. (References, throughout, to a module at the position of 528 or 530 can alternatively mean a module at the position of 528A or 530A, respectively, as well). The LWD module includes capabilities for measuring, processing, and storing information, as well as for communicating with the surface equipment. In embodiments, one or more system parameters of the LWD module can be calibrated as described herein.

The MWD module 530 can also housed in a special type of drill collar, as would be understood by a person of skill in the art in light of the subject disclosure, and can contain one or more devices for measuring characteristics of the drill string and drill bit. The MWD tool can further include an apparatus (not shown) for generating electrical power to the downhole system. This may typically include a mud turbine generator powered by the flow of the drilling fluid, it being understood that other power and/or battery systems may be employed. In aspects, the MWD module can include one or more of the following types of measuring devices: a weight-on-bit measuring device, a torque measuring device, a vibration measuring device, a shock measuring device, a stick slip measuring device, a direction measuring device, or an inclination measuring device.

Figure 6:
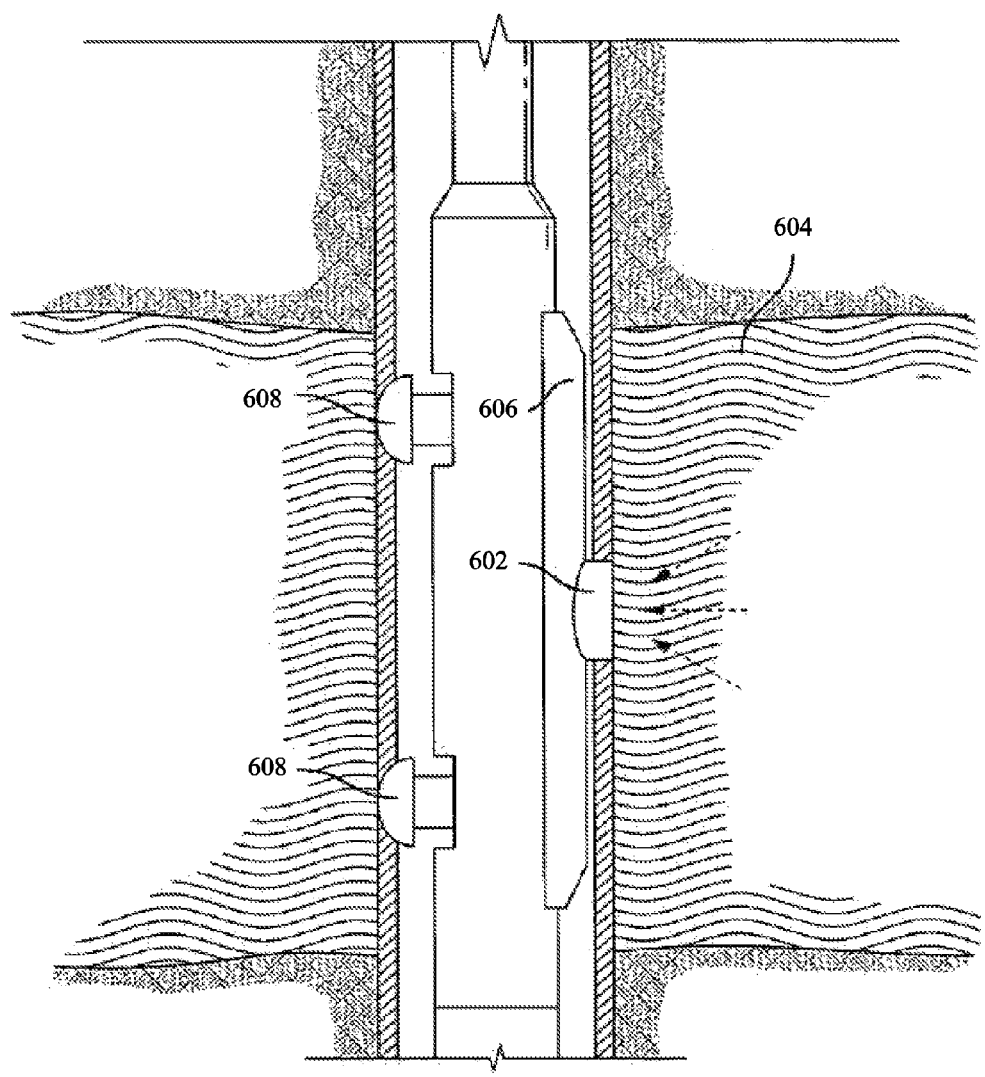
FIG. 6 illustrates a portion of the example while-drilling tool of FIG. 5.

FIG. 6 is a simplified diagram of a sampling-while-drilling logging device of a type described in U.S. Pat. No. 7,114,562, incorporated herein by reference, utilized as the LWD tool 528 or part of an LWD tool suite 528A. The LWD tool 528 can be provided with a probe 602 for establishing fluid communication with the formation and drawing the fluid 604 into the tool, as indicated by the arrows. The probe may be positioned in a stabilizer blade 606 of the LWD tool and extended therefrom to engage the borehole wall. The stabilizer blade 606 can comprise one or more blades that are in contact with the borehole wall. Fluid drawn into the downhole tool using the probe 602 may be measured to determine, for example, one or more of phase behavior or fluid properties. Additionally, the LWD tool 528 may be provided with devices, such as sample chambers, for collecting fluid samples for retrieval at the surface. Backup pistons 608 may also be provided to assist in applying force to push the drilling tool and/or probe against the borehole wall.

The example while-drilling tools shown in FIGS. 3-6 may be used in conjunction with the example methods and systems described herein to obtain measurements and determine thermodynamic properties of fluids. For example, the LWD module 528 and/or the MWD module 530 may include one or more sensors, fluid analyzers and/or fluid measurement units disposed adjacent a flow line and may be controlled by one or both of a downhole control system and a surface-located electronics and processing system to perform at least one of measurements on a fluid sample or calculations related to determining thermodynamic properties of the sample. Additionally, one or more sensors of the LWD module 528 and/or the MWD module 530 may be configured to perform measurements in accordance with systems or methods described herein. One or more other aspects of the LWD module 528 and/or the MWD module 530 may be as described above with reference to the wireline tool 300 shown in FIG. 3 and/or system 100.

Referring now to FIG. 7, there is illustrated a block diagram of a computer operable to execute in conjunction with aspects of the disclosed architecture. In order to provide additional context for various aspects of the subject innovation, FIG. 7 and the following discussion are intended to provide a brief, general description of a suitable computing environment 700 in which various aspects of the innovation can be implemented. While the innovation has been described above in the general context of computer-executable instructions that may run on one or more computers, those skilled in the art will recognize that the innovation also can be implemented in combination with other program modules and/or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, as well as personal computers, hand-held computing devices, microprocessor-based or programmable consumer electronics, and the like, each of which can be operatively coupled to one or more associated devices.

The illustrated aspects of the innovation may also be practiced in distributed computing environments where certain tasks are performed by remote processing devices that are linked through a communications network. In a distributed computing environment, program modules can be located in both local and remote memory storage devices.

A computer typically includes a variety of computer-readable media. Computer-readable media can be any available media that can be accessed by the computer and includes both volatile and nonvolatile media, removable and non-removable media. By way of example, and not limitation, computer-readable media can comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or any other medium which can be used to store the desired information and which can be accessed by the computer.

Communication media typically embodies computer-readable instructions, data structures, program modules or other data in a modulated data signal such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer-readable media.

With reference again to FIG. 7, the exemplary environment 700 for implementing various aspects of the innovation includes a computer 702, the computer 702 including a processing unit 704, a system memory 706 and a system bus 708. The system bus 708 couples system components including, but not limited to, the system memory 706 to the processing unit 704. The processing unit 704 can be any of various commercially available processors. Dual microprocessors and other multi-processor architectures may also be employed as the processing unit 704.

The system bus 708 can be any of several types of bus structure that may further interconnect to a memory bus (with or without a memory controller), a peripheral bus, and a local bus using any of a variety of commercially available bus architectures. The system memory 706 includes read-only memory (ROM) 710 and random access memory (RAM) 712. A basic input/output system (BIOS) is stored in a non-volatile memory 710 such as ROM, EPROM, EEPROM, which BIOS contains the basic routines that help to transfer information between elements within the computer 702, such as during start-up. The RAM 712 can also include a high-speed RAM such as static RAM for caching data.

The computer 702 further includes an internal hard disk drive (HDD) 714 (e.g., EIDE, SATA), which internal hard disk drive 714 may also be configured for external use in a suitable chassis (not shown), a magnetic floppy disk drive (FDD) 716, (e.g., to read from or write to a removable diskette 718) and an optical disk drive 720, (e.g., reading a CD-ROM disk 722 or, to read from or write to other high capacity optical media such as the DVD). The hard disk drive 714, magnetic disk drive 716 and optical disk drive 720 can be connected to the system bus 708 by a hard disk drive interface 724, a magnetic disk drive interface 726 and an optical drive interface 728, respectively. The interface 724 for external drive implementations includes at least one or both of Universal Serial Bus (USB) and IEEE 1394 interface technologies. Other external drive connection technologies are within contemplation of the subject innovation.

The drives and their associated computer-readable media provide nonvolatile storage of data, data structures, computer-executable instructions, and so forth. For the computer 702, the drives and media accommodate the storage of any data in a suitable digital format. Although the description of computer-readable media above refers to a HDD, a removable magnetic diskette, and a removable optical media such as a CD or DVD, it should be appreciated by those skilled in the art that other types of media which are readable by a computer, such as zip drives, magnetic cassettes, flash memory cards, cartridges, and the like, may also be used in the exemplary operating environment, and further, that any such media may contain computer-executable instructions for performing the methods of the innovation.

A number of program modules can be stored in the drives and RAM 712, including an operating system 730, one or more application programs 732, other program modules 734 and program data 736. All or portions of the operating system, applications, modules, and/or data can also be cached in the RAM 712. It is appreciated that the innovation can be implemented with various commercially available operating systems or combinations of operating systems.

A user can enter commands and information into the computer 702 through one or more wired/wireless input devices, e.g., a keyboard 738 and a pointing device, such as a mouse 740. Other input devices (not shown) may include a microphone, an IR remote control, a joystick, a game pad, a stylus pen, touch screen, or the like. These and other input devices are often connected to the processing unit 704 through an input device interface 742 that is coupled to the system bus 708, but can be connected by other interfaces, such as a parallel port, an IEEE 1394 serial port, a game port, a USB port, an IR interface, etc.

A monitor 744 or other type of display device is also connected to the system bus 708 via an interface, such as a video adapter 746. In addition to the monitor 744, a computer typically includes other peripheral output devices (not shown), such as speakers, printers, etc.

The computer 702 may operate in a networked environment using logical connections via wired and/or wireless communications to one or more remote computers, such as a remote computer(s) 748. The remote computer(s) 748 can be a workstation, a server computer, a router, a personal computer, portable computer, microprocessor-based entertainment appliance, a peer device or other common network node, and typically includes many or all of the elements described relative to the computer 702, although, for purposes of brevity, only a memory/storage device 750 is illustrated. The logical connections depicted include wired/wireless connectivity to a local area network (LAN) 752 and/or larger networks, e.g., a wide area network (WAN) 754. Such LAN and WAN networking environments are commonplace in offices and companies, and facilitate enterprise-wide computer networks, such as intranets, all of which may connect to a global communications network, e.g., the Internet.

When used in a LAN networking environment, the computer 702 is connected to the local network 752 through a wired and/or wireless communication network interface or adapter 756. The adapter 756 may facilitate wired or wireless communication to the LAN 752, which may also include a wireless access point disposed thereon for communicating with the wireless adapter 756.

When used in a WAN networking environment, the computer 702 can include a modem 758, or is connected to a communications server on the WAN 754, or has other means for establishing communications over the WAN 754, such as by way of the Internet. The modem 758, which can be internal or external and a wired or wireless device, is connected to the system bus 708 via the serial port interface 742. In a networked environment, program modules depicted relative to the computer 702, or portions thereof, can be stored in the remote memory/storage device 750. It will be appreciated that the network connections shown are exemplary and other means of establishing a communications link between the computers can be used.

The computer 702 is operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, restroom), and telephone. This includes various wireless technologies. Thus, the communication can be a predefined structure as with a conventional network or simply an ad hoc communication between at least two devices.

Wireless technologies allow for connection to the Internet from a couch at home, a bed in a hotel room, or a conference room at work, without wires. Some wireless technologies are similar to that used in a cell phone that enables such devices, e.g., computers, to send and receive data indoors and out; anywhere within the range of a base station. Some wireless technology networks use radio technologies called IEEE 802.11 (a, b, g, etc.) to provide secure, reliable, fast wireless connectivity. Some wireless technology networks can be used to connect computers to each other, to the Internet, and to wired networks (which use IEEE 802.3 or Ethernet). Some wireless technology networks operate in the unlicensed 2.4 and 5 GHz radio bands, at an 11 Mbps (802.11a) or 54 Mbps (802.11b) data rate, for example, or with products that contain both bands (dual band), so the networks can provide real-world performance similar to the basic 10BaseT wired Ethernet networks used in many offices.

What has been described above includes examples of the innovation. It is, of course, not possible to describe every conceivable combination of components or methodologies for purposes of describing the subject innovation, but one of ordinary skill in the art may recognize that many further combinations and permutations of the innovation are possible. Accordingly, the innovation is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A system, comprising:
   a fluid sample container that alters a temperature or a pressure of a fluid sample;
   an optical fluid analyzer (OFA) that determines a compressibility of the fluid sample at each of a plurality of pressures or temperatures, wherein the compressibility comprises an isothermal compressibility $\kappa_T$ or an isentropic compressibility $\kappa_S$, wherein the isothermal compressibility is defined by the equation $$\kappa_T = -\frac{1}{V}\left(\frac{\partial V}{\partial p}\right)_T$$

and the isentropic compressibility is defined by the equation $$\kappa_S = -\frac{1}{V}\left(\frac{\partial V}{\partial p}\right)_S$$

where V is volume, p is pressure, S is entropy, and T is temperature;
   a sound speed component that measures a speed of sound in the fluid sample at each of the plurality of pressures or temperatures; and
   an analysis component that calculates, at each of the plurality of pressures or temperatures, a density of the fluid sample based at least in part on the compressibility and the speed of sound, wherein the analysis component determines one or more thermodynamic properties of the fluid sample based at least in part on the density and the speed of sound, wherein the one or more thermodynamic properties comprises at least one of a property indicative of heat capacity of the fluid sample, a property indicative of an expansivity of the fluid sample, or a property indicative of an adiabatic index of the fluid sample.

2. The system of claim 1, wherein the sound speed component comprises a sonic transducer and a pair of reflectors, and the sound speed component measures the speed of sound based at least in part on a travel time of a pair of sound pulses from the sonic transducer to the pair of reflectors and back to the sonic transducer.

3. The system of claim 1, wherein the OFA measures the compressibility based at least in part on a determination of a change in the area under an absorption peak of a spectrum of the fluid sample.

4. The system of claim 1, wherein the system is implemented at least in part in at least one of a logging while drilling tool or a measurement while drilling tool.

5. The system of claim 1, wherein the system is implemented at least in part in a wireline tool.

6. The system of claim 1, wherein the analysis component determines the one or more thermodynamic properties based at least in part on a numerical integration of the density and the speed of sound over a region of a pressure-temperature space.

7. The system of claim 6, wherein the numerical integration is based on iteration of determinations of derivatives with respect to pressure of the density and a specific heat of the fluid sample, and estimation of the density and specific heat at a greater pressure based at least in part on the derivatives.

8. The system of claim 6, wherein the analysis component represents the density and the speed of sound as polynomial functions with rational exponents.

9. The system of claim 8, wherein the analysis component determines one or more parameters of the polynomial functions based at least in part on regression analysis.

10. A method, comprising:
    capturing a sample of a fluid;
    determining, for each of a plurality of pressures in a range of pressures, a density, a speed of sound, and a heat capacity of the sample, comprising:
      measuring the speed of sound in the sample for each of a plurality of temperatures in a range of temperatures;
      determining a density for the sample for each of the plurality of temperatures, wherein determining the density comprises measuring a compressibility of the sample, the compressibility comprises an isothermal compressibility $\kappa_T$ or an isentropic compressibility $\kappa_S$, wherein the isothermal compressibility is defined by the equation $$\kappa_T = -\frac{1}{V}\left(\frac{\partial V}{\partial p}\right)_T$$

and the isentropic compressibility is defined by the equation $$\kappa_S = -\frac{1}{V}\left(\frac{\partial V}{\partial p}\right)_S$$

where V is volume, p is pressure, S is entropy, and T is temperature; and
      estimating the heat capacity of the sample for each of the plurality of temperatures; and
    determining one or more thermodynamic properties based at least in part on the determined density, the speed of sound, and the heat capacity, wherein the one or more thermodynamic properties comprise at least one of a heat capacity of the sample, an expansivity of the sample, or an adiabatic index of the sample.

11. The method of claim 10, wherein measuring the speed of sound comprises determining a travel time associated with at least one pulse sent from a transducer.

12. The method of claim 10, wherein estimating the heat capacity comprises extrapolating the speed of sound and the density to at least one of pressure values outside the range of pressures or temperatures outside the range of temperatures.

13. The method of claim 10, wherein determining, for each of a plurality of pressures, the density, the speed of sound, and the heat capacity of the sample is based at least in part on measurements taken by a wireline tool.

14. The method of claim 10, wherein determining, for each of a plurality of pressures, the density, the speed of sound, and the heat capacity of the sample is based at least in part on measurements taken by one or more of a measurement while drilling (MWD) or logging while drilling (LWD) tool.

15. The method of claim 10, wherein determining, for each of a plurality of pressures, the density, the speed of sound, and the heat capacity of the sample comprises numerically integrating the density, the speed of sound over at least a subset of the plurality of pressures.

16. The method of claim 15, wherein the numerically integrating comprises:
    determining, at a first pressure the derivative with respect to pressure of the density and the derivative with respect to pressure of the specific heat; and
    estimating, at a second pressure, the density and the specific heat at a greater pressure based at least in part on the density, the specific heat, and the derivatives.

17. The method of claim 10, wherein determining, for each of a plurality of pressures, the density, the speed of sound, and the heat capacity of the sample comprises representing the density, the speed of sound, and the heat capacity as polynomial functions with rational exponents.

18. The method of claim 17, wherein determining, for each of a plurality of pressures, the density, the speed of sound, and the heat capacity of the sample comprises determining one or more parameters of the polynomial functions based at least in part on regression analysis.

19. A system, comprising:
    means for pressurizing and depressurizing a fluid;
    means for measuring a compressibility of the fluid, wherein the compressibility comprises an isothermal compressibility $\kappa_T$ or an isentropic compressibility $\kappa_S$, wherein the isothermal compressibility is defined by the equation $$\kappa_T = -\frac{1}{V}\left(\frac{\partial V}{\partial p}\right)_T$$

and the isentropic compressibility is defined by the equation $$\kappa_S = -\frac{1}{V}\left(\frac{\partial V}{\partial p}\right)_S$$

where V is volume, p is pressure, S is entropy, and T is temperature;
    means for measuring a speed of sound of the fluid; and
    means for determining, based at least in part on the speed of sound and a density of the fluid calculated based on the compressibility and the speed of sound, one or more of a heat capacity of the fluid, an expansivity of the fluid, or an adiabatic index of the fluid.

* * * * *